United States Patent
Bohme et al.

(10) Patent No.: US 7,131,340 B2
(45) Date of Patent: Nov. 7, 2006

(54) DEVICE FOR LOW-VIBRATION FORCE MEASUREMENT IN RAPID DYNAMIC TENSILE EXPERIMENTS ON MATERIAL SAMPLES

(75) Inventors: Wolfgang Bohme, Denzlingen (DE); Manfred Hug, Merdingen (DE)

(73) Assignee: Fraunhofer-Gesellschaft zur Forderung der Angewandten Forschung e.V., Munich (DE)

( * ) Notice: Subject to any disclaimer, the term of this patent is extended or adjusted under 35 U.S.C. 154(b) by 0 days.

(21) Appl. No.: 10/501,980

(22) PCT Filed: Jan. 17, 2003

(86) PCT No.: PCT/EP03/00458

§ 371 (c)(1),
(2), (4) Date: Dec. 30, 2004

(87) PCT Pub. No.: WO03/060481

PCT Pub. Date: Jul. 24, 2003

(65) Prior Publication Data

US 2005/0087023 A1    Apr. 28, 2005

(30) Foreign Application Priority Data

Jan. 18, 2002    (DE)    ................. 102 01 861

(51) Int. Cl.
*G01N 3/00*    (2006.01)
*G01N 3/08*    (2006.01)

(52) U.S. Cl. ............. 73/862.391; 73/862; 73/862.381; 73/862.392; 73/862.393

(58) Field of Classification Search ................ 73/862, 73/856, 827, 808, 788, 828, 831, 862.041, 73/862.042, 862.07, 862.381, 862.391, 862.392, 73/862.393

See application file for complete search history.

(56) References Cited

U.S. PATENT DOCUMENTS

| 3,824,846 A |   | 7/1974 | Andersson |
| 4,107,985 A | * | 8/1978 | Sommer ................ 73/862.633 |
| 5,508,676 A | * | 4/1996 | Grange et al. .................. 338/2 |

FOREIGN PATENT DOCUMENTS

| DE | 30 46 094 A1 | 6/1982 |
| DE | 36 36 252 C2 | 5/1988 |
| DE | 42 04 589 A1 | 8/1993 |

OTHER PUBLICATIONS

International Search Report dated Apr. 28, 2003 for PCT/EP03/00458 (3 pages).

* cited by examiner

*Primary Examiner*—Edward Lefkowitz
*Assistant Examiner*—Freddie Kirkland, III
(74) *Attorney, Agent, or Firm*—Buchanan Ingersoll & Rooney PC

(57) ABSTRACT

A device for force measurement in dynamic tensile experiments on material samples is disclosed. The device includes a force measurement cell in which at least one force measurement sensor is integrated. The force measurement cell has at least one one-piece connecting structure, whereby a material sample may be detachably fixed to the force measurement cell by the connecting structure and the at least one force measurement sensor is arranged on the force measurement cell at a distance from the connecting structure.

12 Claims, 3 Drawing Sheets

DEVICE FOR LOW-VIBRATION FORCE MEASUREMENT IN RAPID DYNAMIC TENSILE EXPERIMENTS ON MATERIAL SAMPLES

TECHNICAL FIELD

The present invention relates to a device for low-vibration force measurement in rapid, crash-relevant dynamic tensile experiments on material samples, comprising a force measuring cell which is integrated in the clamping device and which has at least one force measuring sensor.

STATE OF THE ART

Crash simulations are increasingly employed for calculating in advance the deformation and failure behavior of safety relevant construction and components under crash stress conditions. For example, in the automobile industry, the safety of automobiles in crashes is determined, evaluated and, if need be, improved by means of suited measures of this manner in virtual reality before producing prototypes.

As the reliability of these crash simulations is strongly dependent on the accuracy of the utilized input data, there is an increasing need for more precise and more reliable material data. Of particular interest in this context is precise knowledge of the deformation and failure behavior of materials both in slow, static as well as in, particular, rapid, dynamic stress conditions.

The deformation behavior of technical materials is characterized with the aid of so-called stress-strain curves. They form the basis for calculating the deformation behavior of a component made of the respective material under the influence of external loads. The deformation behavior of various materials and the characteristic stress-strain curves are varyingly dependent on the expansion rate, thus the "rapidity" of the acting load. A one-time load, which in contrast to a static load occurs much faster, is referred to as a dynamic load.

Used as a measure for the "rapidity" of the dynamic load is the so-called expansion rate with a unit of [1/s], thus the relative change in length per period of time. In conventional, standard slow, static tests, for example, expansion rates of about 0.0001/s are set. Compared to this, several million times faster processes with expansion rates of up to 1000/s occur in crash conditions and correspondingly in crash-relevant tests. To illustrate, an expansions rate of 1000/s means that an assumed test length of 1 m would expand within only 1 s to a thousand times its length, thus to 1000 m=1 km. Naturally, in most technical materials failure sets in much earlier, because the material breaks. Due to such dynamic loads as occur in crash conditions, components or samples of material can deform in a very short time (in the range of fractions of milliseconds) to complete failure (fracture).

Determining the material-specific dynamic stress-strain curves is usually by means of rapid tearing tests. As such known quick tearing machines, for example impact machines, are employed to carry out such tests in order to selectively subject correspondingly formed samples of material, which are usually formed as round or flat samples, to slow loads and, in particular, also to rapid dynamic loads.

The forces acting on the material samples during the load phase are measured using force measuring cells. In high load velocities, for example, piezo-force measuring cells are employed for this purpose. Attaching the to-be-tested material sample with the force measuring cell occurs with the aid of an interposed clamping device connected between the actual force-measuring cell and the material sample. In the case of a slow, quasi-static load acting on the material sample, the forces acting inside the material sample can be reliably measured with the aid of this force measuring cell, respectively force measurement arrangement.

With increasing load rates, from experience at expansion rates of more than 1/s, however, it must be noted that these rapid load processes, in particular, also when using quick tearing machines, usually are initiated by a shock load. Inertia forces excite complex elastic wave processes and vibration processes in the force measuring cell, the interposed clamping device and the material sample. These inertia forces ultimately result in difficult to interpret force signals with superimposed vibrations. Depending on the testing facility, very marked superimposed vibrations, which can lead to considerable misinterpretation of the behavior of the material, occur. As a result, the elastic starting part of the stress-strain curve, which is so important for rigidity calculations, and the part of the curve following the starting part, which is so decisive for the course of the deformation and which describes the transition of the test material into the plastic part and is characterized by the technical expansion limit $R_{p0.2}$, can be determined with diminishing precision with an increasing expansion rate.

The goal of a high-speed testing method should therefore be to minimize these superimposed vibrations in order to accurately determine the behavior of the material during a fast, one-time (quick) load. Moreover, the aim is also to precisely measure the behavior of the material despite a quick load and the resulting very short times until fracture occurs (in the following example only very little more than 100 μs=0.0001 s until fracture).

In order to avoid the preceding problem, which occurs, in particular, in testing material samples with expansion rates of more than 1/s, it has been proposed to conduct the force measurement in tensile experiments directly on the test material sample itself with expansion measuring strips, which should be applied at the thicker, only elastically deformed part of the samples. Details of this proposal are found in the following publications: W. Böhme, D.-Z. Sun, W. Schmitt, A. Hönig: Application of Micromechanical Material Models to the Evaluation of Charpy Tests, ASME Symposium: Advances in Local Fracture/Damage Models for the Analysis of Engineering Fracture Problems, Scottsdale, Ariz.:, Scottsdale, Ariz., Apr. 28–May 1, 1992, eds.: J. H. Giovanola and A. J. Rosakis, H00741, pp. 203–216, 1992.

The method drawn from the preceding printed publication regarding the direct application of expansion measuring strips (referred hereinafter to as DMS) on test material samples has also been accepted by European experts, leading to the developments of a European standard, see ESIS document P7-00, Procedure for Dynamic Tensile Tests (2000).

Although precise force measurements can be conducted with the European standard method, in particular in steels with high load rates, application of expansion measuring strips on sometimes very small dimensioned material samples is very complicated and involves quite complicated filigree assembly. This is particularly the case with very small dimensioned material samples taken from components. Often these material samples exist in the form of almost wire-like structures with test diameters of less than 2 mm, and corresponding expansion measuring strips should be applied to their small-dimensioned surfaces. Furthermore, such a type measuring method must be calibrated by means of static preliminary tests at least when a high degree of precision is required, which involves additional testing and measuring.

Finally, this measuring method reaches its limitations in those cases in which plastic deformations occur not only in the test part but also in the thicker part of the sample bearing the applied measuring strips, as in this case there is no longer any linear connection between the measured expansion and the applied force. Such is the case, for example, in materials which have only a small linear-elastic part, such as plastics and magnesium alloys.

DE 36 36 252 C2 describes a dividable grip head with an integrated DMS force transducer to grip the tensile samples suited for gripping tensile samples in a tensile testing machine, impact testing machines or other testing machines. The grip head essentially provides two pressure plates between which a tensile sample in the form of a flat tensile sample is grippable in a non-positive manner in that the pressure plates are pressed together with the aid of a screw mechanism. The two pressure plates are connected to a carrier unit by means of a bolt running through the pressure plates. Force measuring instruments with expansion measuring strips are provided on the pressure plates in the region of this connecting bolt. Applying a load to the tensile sample clamped between the pressure plates creates tensile stress-strain proportional to the tensile force that is transmitted to the bolt and is determined with the aid of measuring the expansion measuring strips. However, particularly, in quick tensile tests characterized by sudden tearing in the tensile sample, it turned out that especially in the region of the points of connection, such as the bolt connection, due to the existent connection gap, additional local impact loads and, therefore, inertia forces occur, which cause excessive local tensions and vibrations that falsify the measuring results. Conducting a local force measurement directly at such points of connection has the disadvantage that such local contact problems effect the measuring signal over-proportionally strongly and therefore effect it negatively.

SUMMARY OF THE INVENTION

Thus the object of the present invention is to design a device for force measurement in dynamic tensile experiments on material samples, comprising a force measuring cell, in which at least one force measuring sensor is integrated in such a manner that a highly precise low-vibration force measurement is possible when conducting dynamic tensile experiments on material samples up to high, crash relevant expansion rates, thus up to approximately 1000/s, without the aforedescribed complex time-consuming technical measuring and assembly. But rather, the object is to provide a device which provides measuring results of approximately the same measuring quality as the European standard procedures described in the preceding but with considerable less technical effort.

The solution to the object of the present invention is disclosed herein. Features that advantageously further develop the inventive idea are described in the following description with reference to the preferred embodiments.

A key element of the present invention is that a device for force measurement in dynamic tensile experiments on material samples, comprising a force measuring cell in which at least one force measuring sensor is integrated, is designed in such a manner that the force measuring cell is executed one-piece with at least one first connecting structure via which the material sample is connectable directly with the force measuring cell. The at least one force measuring sensor is disposed at a distance from the first connecting structure in such a manner that even vibrations excited in the connecting structure by local contact problems or by inertia forces can only influence the measuring signal very little. Despite being spaced a distance from the connecting structure, the preferably two or more force measuring sensors disposed on the force measuring cell are only a small as possible distance from the material sample held in the connecting structure.

The idea on which the present invention is based relates to the integration of the force measuring cell in the clamping device, respectively vice versa, permitting a compact as possible manner of construction of an invented force measuring cell. In this way, the force sensors are disposed as near as possible to the test material sample. Vibrating masses, such as for example in the piezo-force measuring cell described in the introduction can thus be largely avoided so that disturbances which lastingly negatively influence measuring results can be almost completely ruled out.

In a first possible embodiment, the force measuring cell designed according to the present invention comprises a one-piece housing part which provides at least one connecting structure for firm, detachable connection with a material sample.

In a preferred embodiment for round tensile samples, the connecting structure is designed as a screw connection with an inner thread inside the housing of the force measuring cell. A corresponding counter thread, which is provided in a suited manner on the material sample, can be screwed into this inner thread. In this manner, it is possible to bring the housing of the force measuring cell in direct, firm, detachable contact with the test material sample, completely obviating any intermediate elements as known from the prior art. As another described preferred embodiment shows, the force measuring sensors in the form of expansion measuring strips are applied to the exterior of the housing to receive the measuring signals.

In order to attach the force measuring cell to a firm back-rest, the force measuring cell is provided with a sturdier, respectively more massive, part of the housing compared to the more thin-walled housing structure in the region of the first connecting structure and in the region where the force measuring sensors are attached. The end of the housing opposite the first connecting structure, thus the second connecting structure of the force measuring cell, is preferably provided with an outer thread via which the force measuring cell is firmly connectable to a stationary base plate of the testing machine. Alternative connecting methods for firm connection of the force measuring cell with the testing machine are, of course, also feasible such as, for example, bolt and flanged connections, which are preferably employed in testing flat band-like material samples. For single force action, the vacant end of the sample opposite the force measuring cell is firmly connected with the moveable part of a load facility, for example a quick tearing machine.

In a preferred embodiment, provided for reception of the measuring signals are four expansion measuring strips attached symmetrically to the housing. In order to increase measuring precision, to detect and, if need be, to compensate the bending fractions, these four expansion measuring strips are attached to the housing facing each other respectively. As, when testing round tensile samples, the housing is designed largely axially symmetrically as a harp, symmetrical attachment of the force measuring sensors to the housing in the form of expansion measuring strips is suitable. If three, four or even more force measuring sensors, which are correspondingly miniaturized, are evenly distributed in one or a multiplicity of cross sectional planes about the housing, permits nearly total detection of the spatial deformation of the housing and thus of the material sample during the tensile experiment, yielding highly precise measuring results.

Dimensioning of the housing and selection of the material of the housing of the force measuring cell depends fundamentally on the rigidity of the test material sample, respectively of the test material. For testing metals, titanium alloys have proven to be particularly suited as a material for the housing. However, in addition to the selection of the material, the structural design of the housing of the force measuring cell is also decisive for its rigidity. Thus, on the one hand, the housing must be designed distinctly more rigid than the material sample, on the other hand the housing, however, must be designed pliant enough that sufficiently large deformations occur within the housing, which can be detected with the applied expansion measuring strips.

BRIEF DESCRIPTION OF THE DRAWINGS

The present invention is made more apparent in the following, without the intention of limiting the scope or spirit of the inventive idea, using preferred embodiments with reference to the accompanying drawings.

WAYS TO CARRY OUT THE INVENTION, COMMERCIAL APPLICABILITY

Figure 1:
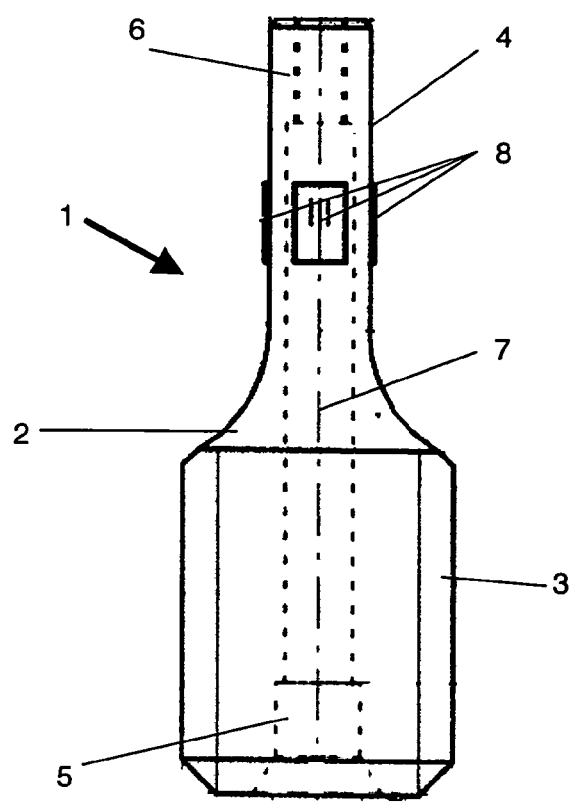
FIG. 1 shows a schematic lateral view of a force measuring cell.

FIG. 1 shows a lateral view of an advantageously designed force measuring cell 1, comprising a one-piece housing 2. The housing 2 has a cylindrically shaped section 3 with an outer thread adjoined to which in a conically tapering manner is a second cylindrically shaped section 4. The housing 2 is fabricated from a solid material and can be produced as a harp. Preferably, very strong titanium alloys are suited as the material for the housing. For the purpose of attaching the force measuring cell 1, for example, to a fixed back-rest, there is the outer thread in section 3. Preferably, a central bore 5 serves to simply adapt structurally to the rigidity of the cell in the region 4, which is obtained by suited selection of the inner and outer diameters. In the same manner, the cylindrically shaped section 4 of the force measuring cell 1 is provided with a connecting structure formed as an inner thread, into which an outer thread of a material sample (not depicted) can be firmly but detachably screwed. In addition, four expansion measuring strips 8 arranged symmetrically to the symmetric axis 7 of the force measuring cell are provided on the outer contour of the cylindrically shaped region 4 of the force measuring cell, in which for the purpose of attaching the material sample a connecting structure 6 in the form of an inner thread is provided. Due to the tapering outer contour in the outer diameter in region 4, the housing 2 is able to follow to a limited degree the deformations induced in the housing in this region 4 when load is put on the material sample in the housing 2 in such a manner that the housing deformations can be detected with high precision by the expansion measuring strips 8.

Even very rapid deformations are directly transferred via the material sample into the region 4 of the force measuring cell 1 without being influenced by the resonant vibration behavior of the adjacent parts of the clamping device and the coupled force measuring cells or their oscillations.

Figure 3:
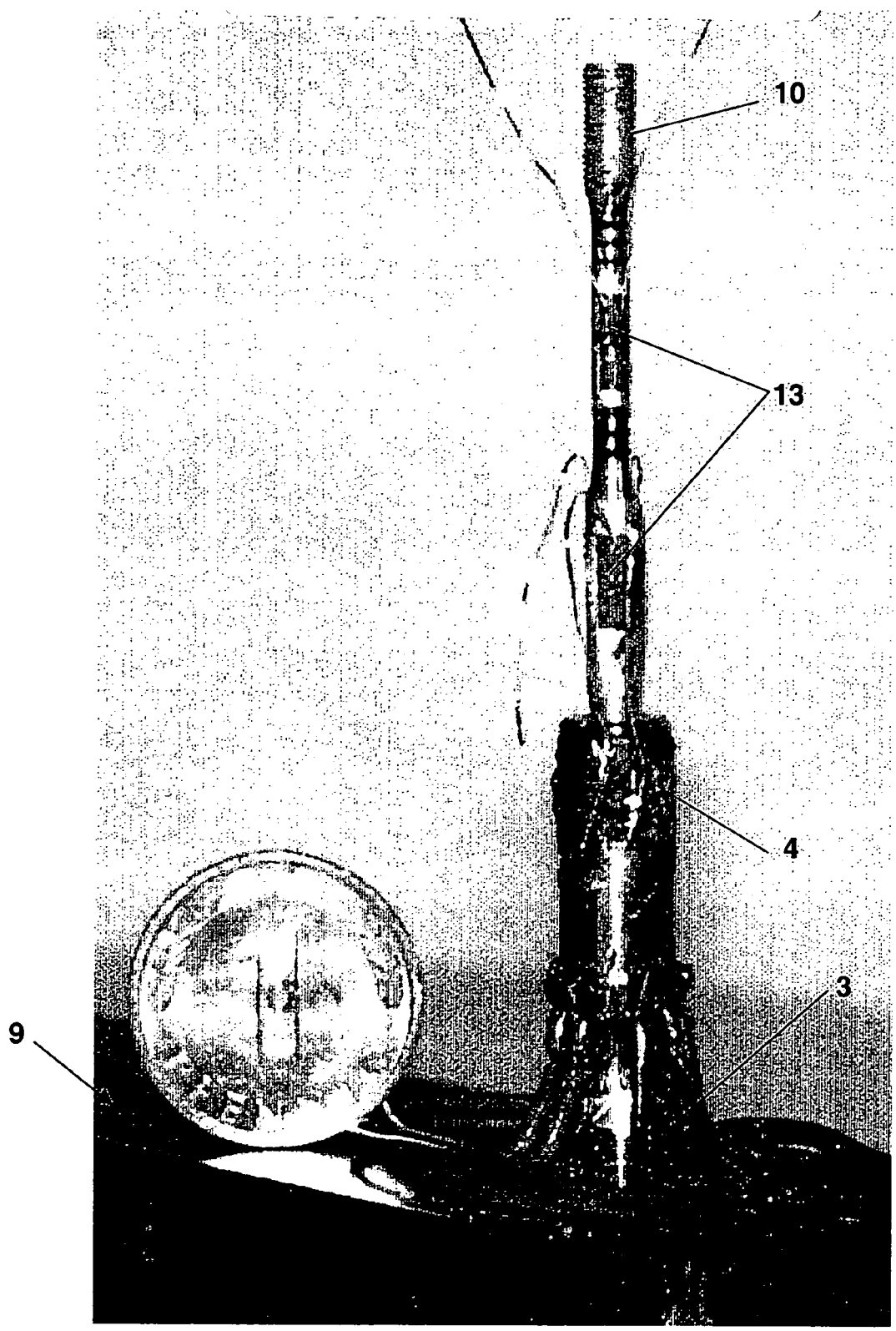
FIG. 3 shows a photographic representation of a preferred embodiment of a force measuring cell.

FIG. 3 shows a photographic representation of a real force measuring cell 1 especially for testing mini-round tensile samples with testing diameters of less than 2 mm, which is connected with its region 3 in a firm, detachable manner to a fixed back-rest 9.—It is noted only for the sake of completeness that the samples may be dimensioned larger if sufficient material is available, with a testing diameter of 4–8 mm, the samples are designed correspondingly longer. A correspondingly larger dimensioned force measuring cell should be employed for such type samples as well.—A material sample 10 to be tested in a dynamic tensile experiment is connected in a firm, detachable manner to the region 4 of the force measuring cell 1. This is a mini-round sample which is fabricated from a magnesium alloy AM50. To carry out the dynamic tensile experiment, a corresponding quick tearing machine, respectively a corresponding impact machine (not depicted), is coupled to the top end of the material sample 10. The coin beside the force measuring cell demonstrates the dimensions of the force measuring cell, which has a very small, compact type of construction of a few centimeters.

Only for the purpose of providing a complete description of the components shown in FIG. 3, it is pointed out that the expansion measuring strips 13 are attached directly to the material sample 10. Filigree-like yet-to-be-connected electric connecting wires lead from expansion measuring strips 13. The measuring strips in the thin test part of the sample are for highly-precise expansion measurements up to approximately 1% expansion. The measuring strips applied in the thicker part of the samples are additionally attached in order to simultaneously conduct a force measurement corresponding to the proposed European standard compared with the new measuring cell (see results in FIG. 2). The invented force measuring cell obviates these last mentioned measuring strips. The figure demonstrates the complicated application of such type expansion strips to the surface of the material sample 10.

Figure 2:
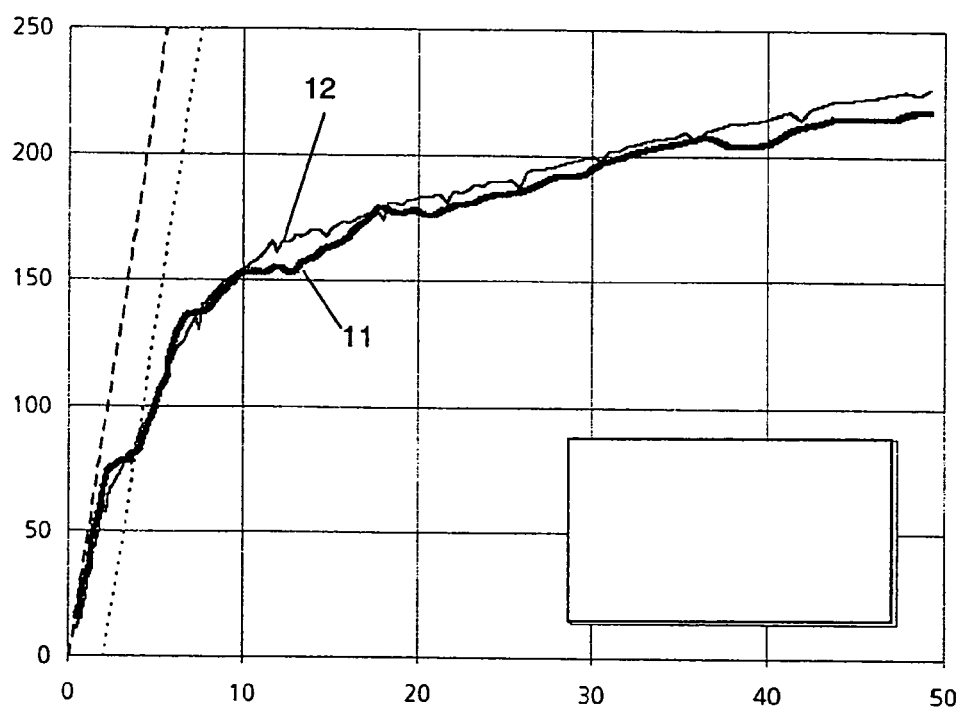
FIG. 2 shows characteristic stress-strain curves.

The forces for determining the tensions in the dynamic stress-strain curves shown in FIG. 2 are determined with the real test arrangement shown in FIG. 3. The material sample is torn with a trigger velocity of the quick tearing machine of v=5 m/s and an expansion rate resulting therefrom of about 500/s. The diagram shown in FIG. 2, along the abscissa of which the expansion of the material sample is plotted in [$^0/_{00}$] and along the ordinates of which, the tension is plotted in megapascal [Mpa], the diagram course 11 represents the stress-strain curve of material sample 10 recorded with the aid of the force measuring cell designed according to the present invention. To demonstrate the measuring quality of the measuring curve 11, a second stress-strain curve 12 is plotted in the diagram in FIG. 2 obtained with the substantially more complicated sample instrumentation in connection with a statically determining, nonlinear calibrating curve, a method which represents an extension of the European standard described in the introduction. To be noted is that the expansions of the material sample up to approximately 1% expansion are based on the expansion measuring strip measurement in the thin test part of the sample, following this the expansion measurement is based on high-velocity photograph measurements.

The measuring results shown in FIG. 2 demonstrate that it is also possible to obtain high quality of the state-of-the-art measurement using the invented force measuring cell (see measuring curve 11) with substantially less effort. Only for the purpose of completeness, it is pointed out that the broken straight line represents Hook's straight line for linear material behavior, whereas the dotted straight line represents an auxiliary line offset 0.2% thereto, whose intersection with the measured stress-strain curve corresponds by way of definition to the technical expansion limit $R_{p0.2}$, which like the stress-strain curve generally also depends on the expansion rate. In the present case, the dynamic expansion limit for an expansion rate of 500/s can be determined.

The invented force measuring cell also permits, in particular, detection in the starting region near the origin of the coordinates according to the diagram representation in FIG. 2 with high precision and largely uninfluenced by superimposed vibrations. In particular, the dynamic E module of the respective material can also be determined from the starting incline.

Figure 4:
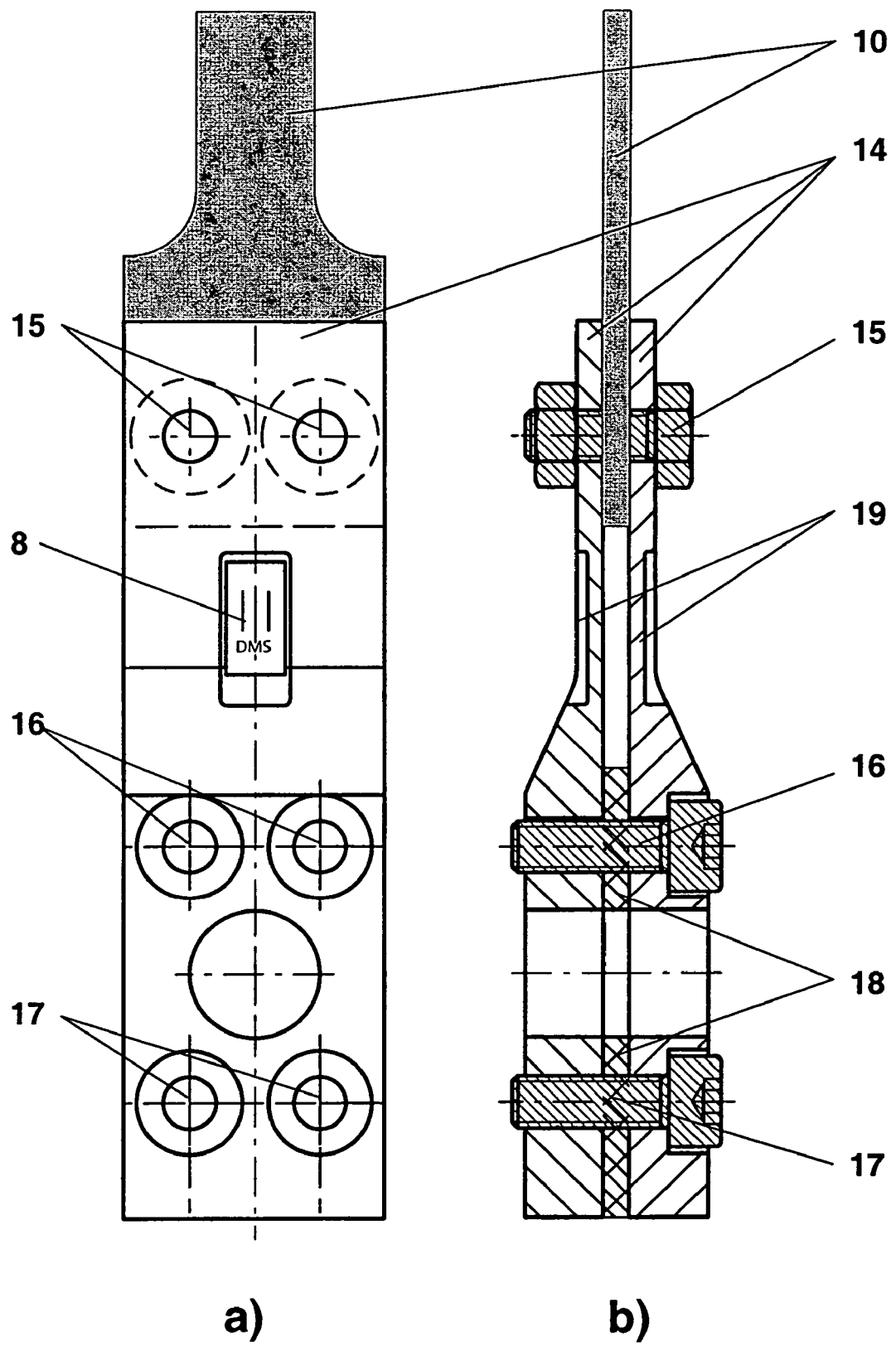
FIGS. 4a and 4b shows a front and a lateral view of a force measuring cell for testing flat tensile samples.

Another alternative force measuring cell for testing flat tensile samples is shown in FIGS. 4a and b, which represent a front view and a lateral view respectively.

The force measuring cell has two pressure plates 14. Both pressure plates 14 can be firmly connected by means of screw connections 15, 16, and 17. In the lower region of the force measuring cell, a spacer 18 is inserted between the two pressure plates 14. The thickness of the spacer 18 is the same as that of the test flat tensile sample 10, which is inserted between the two pressure plates 14. The two screw connections 15 represent the first connecting structure with which the test flat tensile sample 10 can be clamped between the two pressure plates 14. At a distance therefrom, expansion measuring strips (DMS) 8 for receiving the measuring signals are attached to the outer side of the pressure plates 14.

The top region of the pressure plates 14, in which the flat tensile probe 10 is insertable, is designed thin-walled compared to the lower region. In this manner, the forces acting on sample 10 are registered with the highly sensitive expansion measuring strips 8. In the present preferred embodiment, the latter are integrated in the recesses, respectively the indentations (19), in the pressure plates 14 to protect them with covering means. Compared to this, the lower region of the pressure plates 14, the second connecting structure, is designed as massively as possible so that this region is designed as low-vibrating as possible and is connectable to a fixed back-rest.

The invented design of the force measuring cell has the following advantages over the state of the art:
- no or extremely low oscillations in the measuring signals detectable with the force measuring cell,
- measuring accuracy of the invented force measuring cell is comparable to the much more complicated sample instrumentation according to the European standard,
- reduced complexity and therefore reduced costs, because no sample instrumentation is required,
- reduced complexity and therefore reduced costs, because no static calibrating tests with instrumented sample are required,
- simple handling and use of the invented force measuring cell, compared to static force measuring cells,
- the force measuring cell can also be used for materials without a marked linear-elastic starting region, such as for example for magnesium alloys or plastics where measuring with the sample instrumentation according to the European standard and use of linear calibration factors failed, the construction and measuring principle is readily applicable for various dynamic testing arrangements, such as for example round tensile samples or flat tensile samples of various sizes.

LIST OF REFERENCE NUMBERS

| | |
|---|---|
| 1 | force measuring cell |
| 2 | Housing |
| 3, 4 | cylindrically shaped housing region |
| 5 | Bore |
| 6 | inner thread |
| 7 | axis of symmetry |
| 8 | force measuring sensor, expansion measuring strip |
| 9 | fixed back-rest |
| 10 | material sample, flat tensile sample |
| 11 | measuring curve, registered with the invented force measuring cell |
| 12 | measuring curve according to the state of the art |
| 13 | expansion measuring strip instrumentation according to proposed ESIS standard P7-00 |
| 14 | pressure plate |
| 15 | screw connection |
| 16 | screw connection |
| 17 | screw connection |
| 18 | Spacer |
| 19 | recess |

The invention claimed is:

1. A device for force measurement in dynamic tensile experiments on material samples, comprising a force measuring cell, in which at least one force measuring sensor is integrated and which is executed one piece with a first connecting structure, with the material sample being connectable in a firm, detachable manner via said first connecting structure with said force measuring cell, which is provided with a second connecting structure, which is disposed opposite said first connecting structure and via which said force measuring cell is attachable to a fixed back-rests, wherein at least two force measuring sensors are disposed on said force measuring cell spaced from said first connecting structure in such a manner that the distance between said at least two force measuring sensors and said first connecting structure, and between said at least two force measuring sensors and the tensile sample, is smaller than the distance between said at least two force measuring sensors and said second connecting structure, said force measuring cell is provided with a housing or with two pressure plates, which has, respectively have, a thinner wall thickness in the region of said force measuring sensors than in the other housing region or other regions of said pressure plates, and said force measuring cell has more a stable type of construction regarding elastic deformability in the region of said second connecting structure than in the region of said first connecting structure and said at least two force measuring sensors.

2. The device according to claim 1, wherein said first connecting structure is a screw connection, having provided on said force measuring cell a thread contour into which a counter thread provided on the material sample is insertable in a firm, detachable manner.

3. The device according to claim 2, wherein:
said two pressure plates of said force measuring cell can be pressed against each other by means of firm, detachable pressure means,
the tensile sample can be pressed between said pressure plates with force, and
said at least one force measuring sensor is disposed on said pressure plates at a distance from said pressure means.

4. The device according to claim 2, wherein said housing is designed axially symmetrical to an axis of symmetry along which the tensile force acts on said force measuring cell via said material sample.

5. The device according to claim 1, wherein said first connecting structure is a flange or bolt connection, and on the material sample a corresponding counter flange is provided, respectively a connecting contour corresponding to said bolt connection.

6. The device according to claim 5, wherein:
said two pressure plates of said force measuring cell can be pressed against each other by means of firm, detachable pressure means,
the tensile sample can be pressed between said pressure plates with force, and
said at least one force measuring sensor is disposed on said pressure plates at a distance from said pressure means.

7. The device according to claim 5, wherein said housing is designed axially symmetrical to an axis of symmetry along which the tensile force acts on said force measuring cell via said material sample.

8. The device according to claim 1, wherein:
said two pressure plates of said force measuring cell can be pressed against each other by means of firm, detachable pressure means,
the tensile sample can be pressed between said pressure plates with force, and
said at least one force measuring sensor is disposed on said pressure plates at a distance from said pressure means.

9. The device according to claim 8, wherein said housing is designed axially symmetrical to an axis of symmetry along which the tensile force acts on said force measuring cell via said material sample.

10. The device according to claim 1, wherein said housing is designed axially symmetrical to a axis of symmetry along which the tensile force acts on said force measuring cell via said material sample.

11. The device according to claim 10, wherein said at least two force measuring sensors are applied on said housing in a symmetrical arrangement relative to said axis of symmetry.

12. The device according to claim 1, wherein said force measuring cell contains titanium.

* * * * *